US012371397B2

(12) United States Patent
Daly

(10) Patent No.: US 12,371,397 B2
(45) Date of Patent: Jul. 29, 2025

(54) ETHYL BENZYL QUATERNARY AMINES OF AMIDO AMINES FOR IMPROVED ANTIFUNGAL PROPERTIES

(71) Applicant: Thomas P. Daly, Arlington Heights, IL (US)

(72) Inventor: Thomas P. Daly, Arlington Heights, IL (US)

(73) Assignee: TPAT IP, Arlington Heights, IL (US)

( * ) Notice: Subject to any disclaimer, the term of this patent is extended or adjusted under 35 U.S.C. 154(b) by 23 days.

(21) Appl. No.: 18/233,307

(22) Filed: Aug. 12, 2023

(65) Prior Publication Data
US 2023/0382844 A1 Nov. 30, 2023

Related U.S. Application Data

(60) Division of application No. 17/370,992, filed on Jul. 8, 2021, now abandoned, which is a continuation of application No. 16/430,497, filed on Jun. 4, 2019, now abandoned, which is a continuation of application No. 15/725,757, filed on Oct. 5, 2017, now Pat. No. 10,308,589, which is a continuation-in-part of application No. 14/969,920, filed on Dec. 15, 2015, now Pat. No. 9,802,908.

(60) Provisional application No. 62/094,741, filed on Dec. 19, 2014.

(51) Int. Cl.
C07C 211/63 (2006.01)
C07C 233/36 (2006.01)

(52) U.S. Cl.
CPC .......... *C07C 211/63* (2013.01); *C07C 233/36* (2013.01)

(58) Field of Classification Search
CPC ............................ C07C 211/63; C07C 233/36
USPC ......................................................... 562/568
See application file for complete search history.

(56) References Cited

FOREIGN PATENT DOCUMENTS

JP       2004083562    *  3/2004
RO          91907      * 12/1987

OTHER PUBLICATIONS

Ge et al. Langmuir (2013), 29(47), 14411-14420.*
Machine translation JP2004083562, 2004.*

* cited by examiner

Primary Examiner — Ana Z Muresan
(74) Attorney, Agent, or Firm — Clifford Kraft

(57) ABSTRACT

Ethyl benzyl quaternaries having superior anti-fungal properties versus their benzyl quaternary analogs. The ethylbenzyl amidoamine quaternaries of the present invention are easily produced without significant waste and with minimal capital, while possessing improved antimicrobial properties. These molecules are useful in a range of applications such as fungicides, personal care as treatments for acne, dandruff, psoriasis and other fungal skin born conditions, as well as in feminine products where an antifungal is required that is gentle on the sensitive tissues, as well as HIV prevention. These molecules are also excellent hair conditioners and laundry fabric softeners.

3 Claims, 7 Drawing Sheets

ETHYL BENZYL QUATERNARY AMINES OF AMIDO AMINES FOR IMPROVED ANTIFUNGAL PROPERTIES

This application is a divisional of application Ser. No. 17/370,992 filed Jul. 8, 2021 and is related to, and claims priority from, U.S. Provisional patent application No. 62/094,741 filed Dec. 19, 2014. Application Ser. No. 17/370, 992 and 62/094,714 are hereby incorporated by reference in their entireties.

BACKGROUND

Field of the Invention

The present invention relates to the field of amines, quaternary amines and more particularly to ethylbenzyl (EB) quaternary amines.

Description of the Problem Solved by the Invention

Quaternary amines are very useful compounds as cationic surfactants, corrosion inhibitors, personal care emollients, electrolytes and antimicrobials. Typical methyl and benzyl quaternary amines are typically much more antibacterial than antifungal, and have little effect against spores. Ethyl Benzyl quaternaries (quats) have much greater fungal and spore efficacy, as well as effectiveness against viruses, and mycobacteria. The production of many such ethyl benzyl quats require a large investment in high pressure equipment to produce the tertiary amines needed as precursors. The present invention utilizes fatty acids and amines with both a primary and tertiary amine group, or a secondary and a tertiary amine group. The readily available nature and cost effectiveness of these amines makes these products not only more effective, but also cost effective to the smaller chemical manufacturer.

SUMMARY OF THE INVENTION

The present invention relates to ethylbenzyl chloride quats (EB quats) and their related salts. The synthesis of EB quats requires minimal capital requirements, produces products in good yields, without difficult to dispose of waste and in a cost effective manner. The preferred embodiment of the invention is to perform a condensation reaction of a linear or branched, saturated or unsaturated fatty acid, of between 2 and 22 carbons with an amine that has either a primary amine and tertiary amine or a secondary amine and tertiary amine. The example used herein will be dimethylaminopropylamine (DMAPA), but the invention is not limited to DMAPA but to any amine as described. The amido amine that results from the condensation reaction described is then reacted with ethyl benzyl chloride (EBC) to produce the desired EB quat. Additional processing, such as ion exchange can be performed to eliminate the chlorine or substitute it for another anionic species, organic or inorganic. Acetates are the simplest organic salt of the EB quats. Propionates and butyrates result in even greater antifungal properties than the chloride salts.

SUMMARY OF THE INVENTION

The reaction of ethylbenzyl chloride with amidoamines produces EB quats that are superior to their methyl and benzyl quat analogs in that they are more antifungal and antiviral. The invention disclosed herein is a cost effective way to make quaternaries that are mild to the skin, non-hazardous and have multiple uses. Applications for such quaternaries are in personal care as a treatment for acne, dandruff, psoriasis, and other skin born bacterial or fungal maladies. Additionally, the EB quats are much improved fungicides and sporicides for use in agriculture. In oilfield applications, the EB quats are useful as surface treatments for clays, such as bentonite, and as corrosion inhibitors and power improvers.

DETAILED DESCRIPTION OF THE INVENTION

Figure 1:
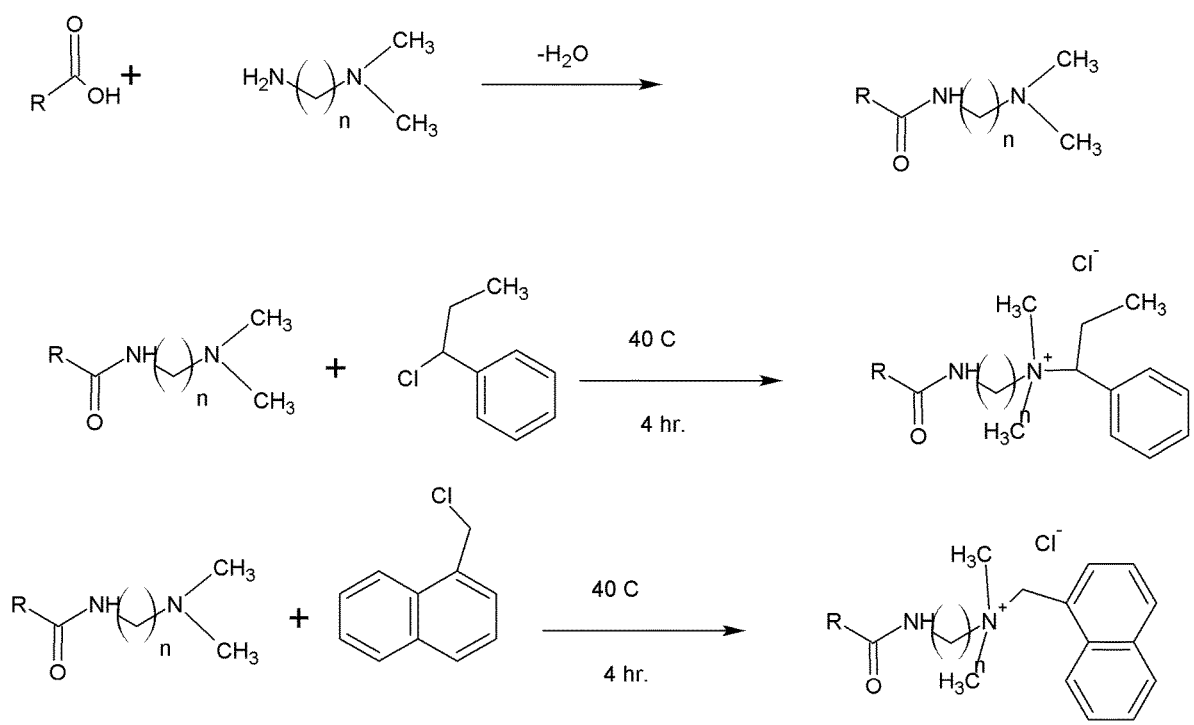
FIG. 1 shows the synthesis of EB quaternary from amidoamines, n is an integer. R is alkyl, linear or branched, saturated or unsaturated, cyclic or acylic from 1 to 21 carbons.
Figure 2:
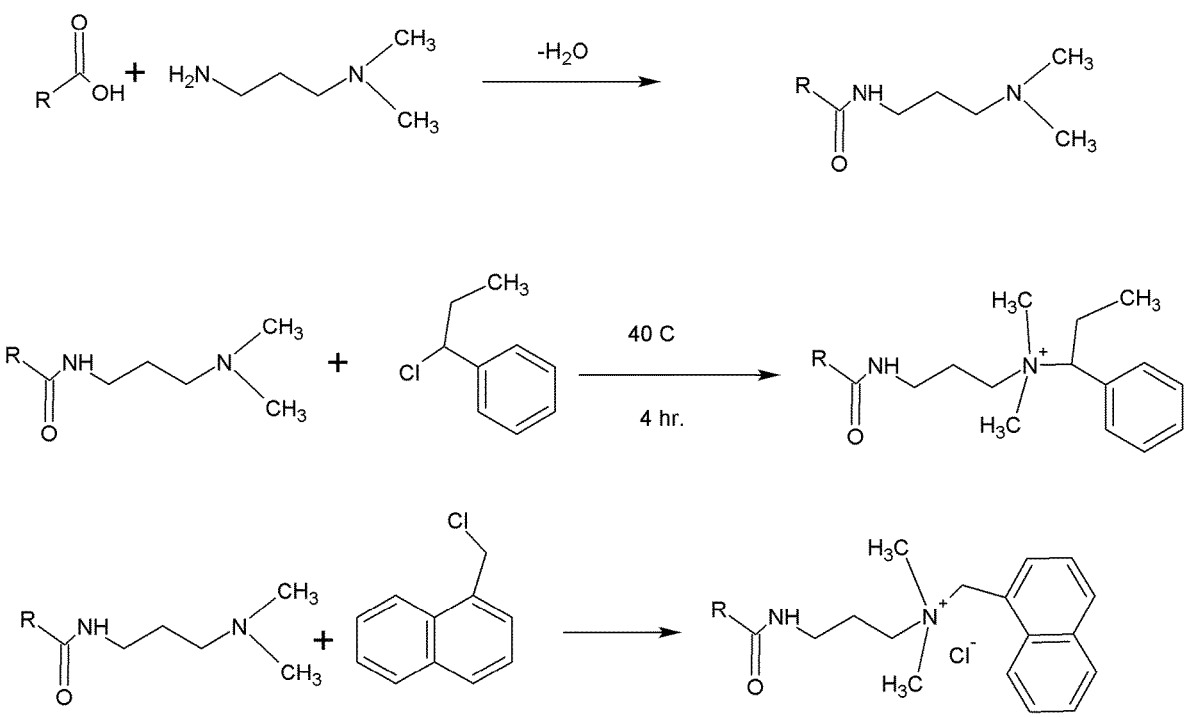
FIG. 2 shows the use of dimethylpropylamine as the amidoamine. R is alkyl, linear or branched, saturated or unsaturated, cyclic or acylic from 1 to 21 carbons.
Figure 3:
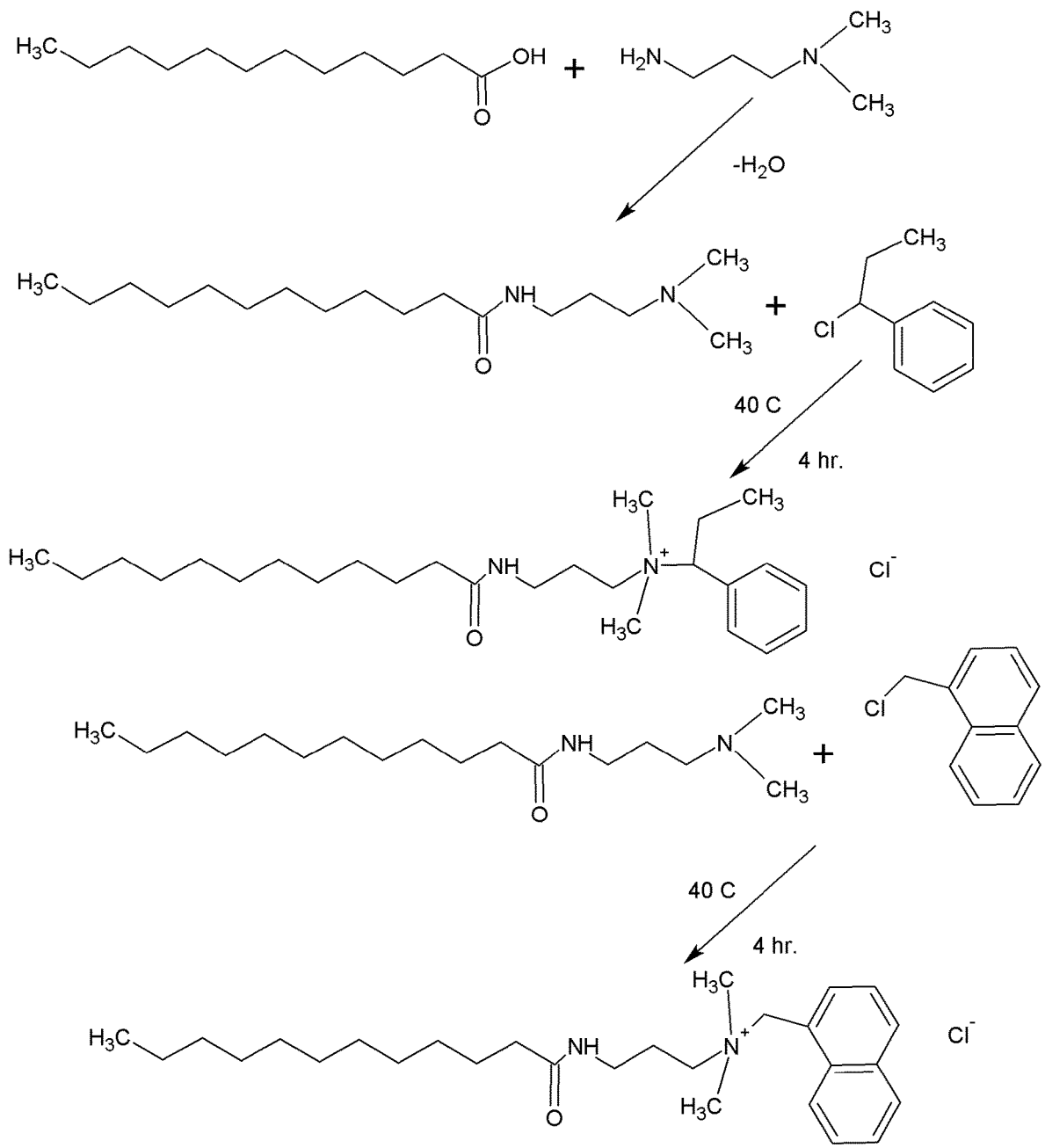
FIG. 3 shows the amidoamine quaternary from lauric acid and DMAPA. R is alkyl, linear or branched, saturated or unsaturated, cyclic or acylic from 1 to 21 carbons.
Figure 4:
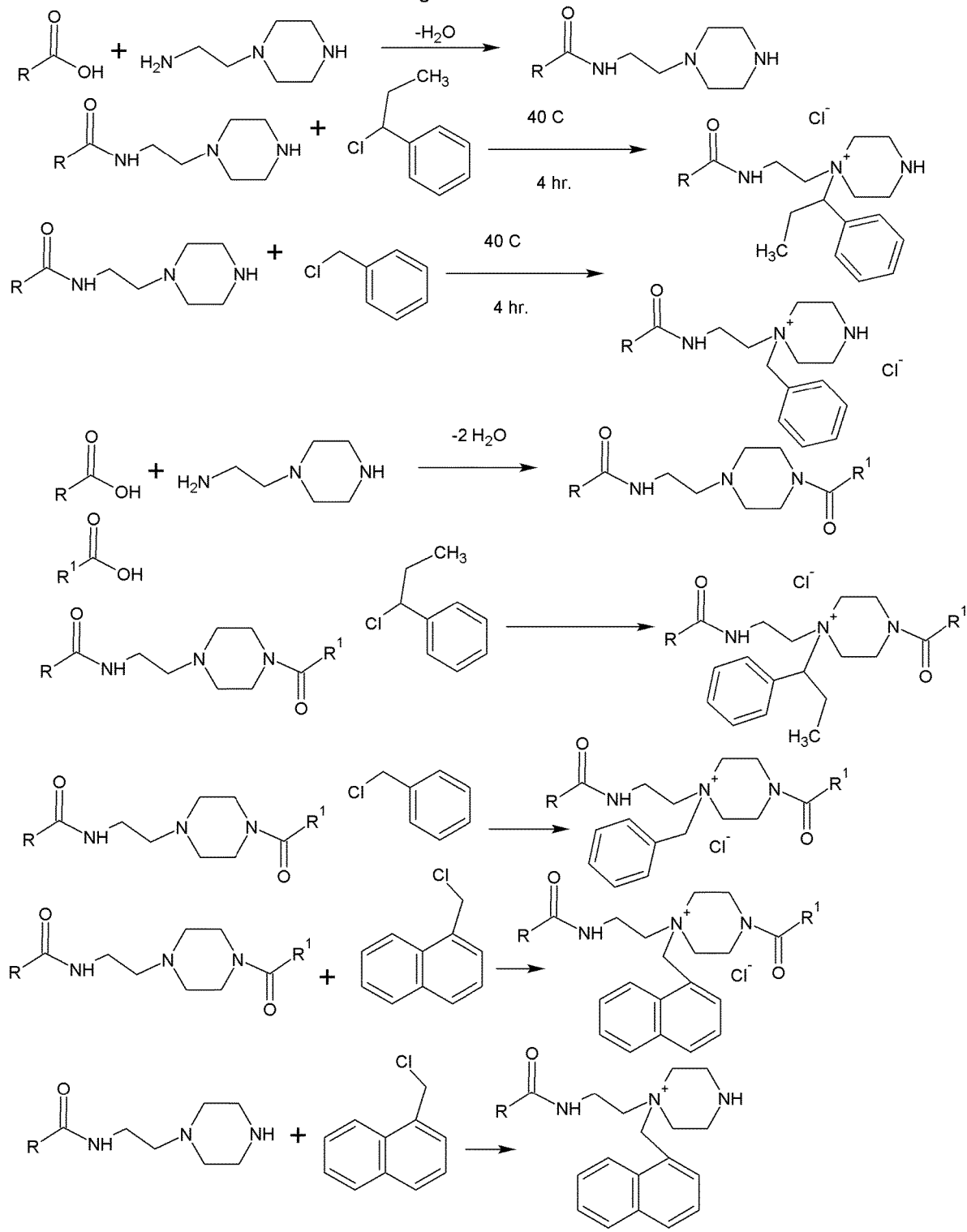
FIG. 4 shows the use of aminoethylpiperadine as the diamine. R and $R^1$ are independently chosen from alkyl, linear or branched, saturated or unsaturated, cyclic or acylic from 1 to 21 carbons.
Figure 5:
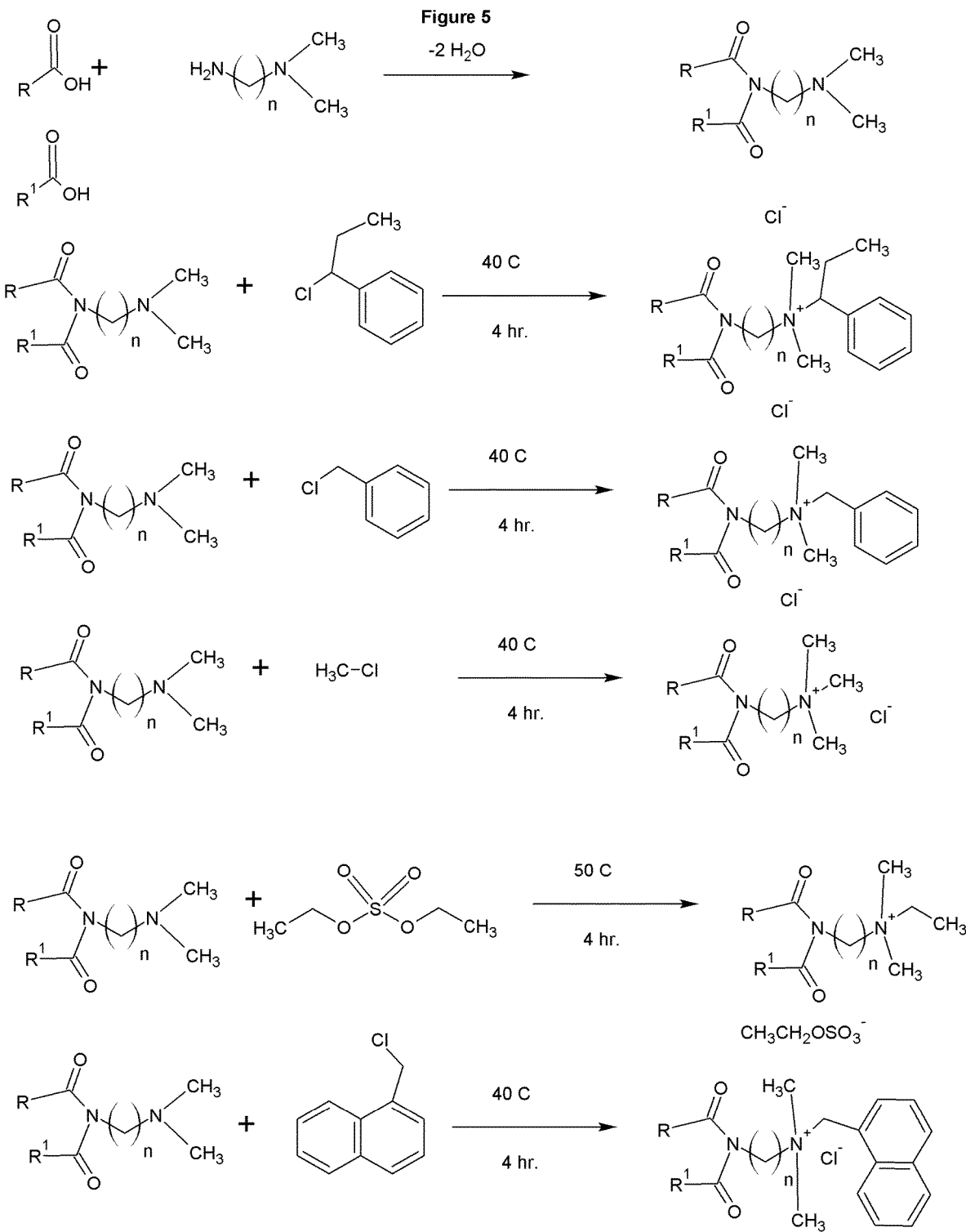
FIG. 5 shows the synthesis of dialkyl amidoamine quaternaries. R and $R^1$ are independently chosen from alkyl, linear or branched, saturated, cyclic or acylic or unsaturated from 1 to 21 carbons.

Ethyl benzyl quaternaries (EB quats) and their salts, as well as salt free EB quats offer a distinct advantage over methyl and benzyl quaternaries. The EB quats have superior anti-fungal performance and, the amidoamine quats, can be made in cost effective manner with minimal capital. FIG. 1 shows the general principle, showing a linear, alkyl diamine, but this need not be the case. However, the preferred embodiment of the invention is the condensation of fatty acid and dimethylaminopropyl amine (DMAPA), followed by reaction with ethyl benzyl chloride as shown in FIGS. 2 and 3. Other diamines and even other polyamines so long as a primary or secondary amine is present and a tertiary amine. Another example would be the use aminoethylpiperadine as shown in FIG. 4. FIG. 5 shows the synthesis of dialkyl amidoamine quaternaries. The diamido compounds are stearically hindered and thus, more difficult to prepare. A longer reaction time is required to reach the diamide as the temperature must be mostly held at around 80 C under about 20 LB of vacuum. Higher temperatures in the DMAPA case, will lead to loss of DMAPA. Activated forms of fatty acids may also be utilized, such as acid chlorides (sufficient base neutralization must occur during the reaction or sufficient base must be present before the reaction to neutralize the HCl generated and prevent amine neutralization. Aldehydes may also be used. Starting from oils did result in some diamide, but not in sufficient quality versus the longer the reaction time. The ethyl quaternary is formed with an ethyl sulfate salt for the purposes of demonstrating that various counter anions are possible and all are within the scope of the invention.

Figure 6:
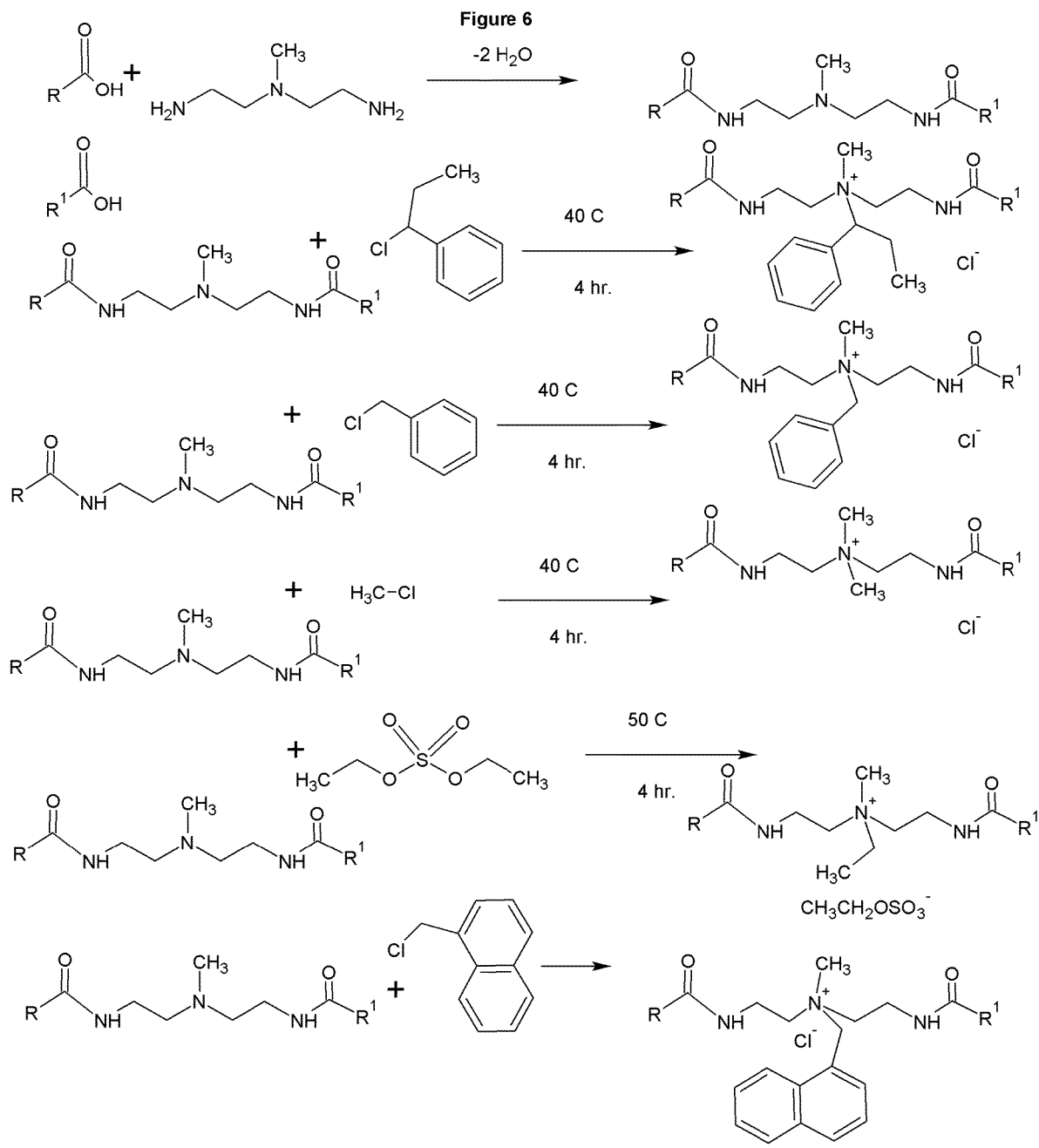
FIG. 6 shows the synthesis of dialkyl quats from N,N-Bis(2-aminoethyl)methylamine. R and $R^1$ are independently chosen from alkyl, linear or branched, saturated or unsaturated, cyclic or acylic from 1 to 21 carbons.
Figure 7:
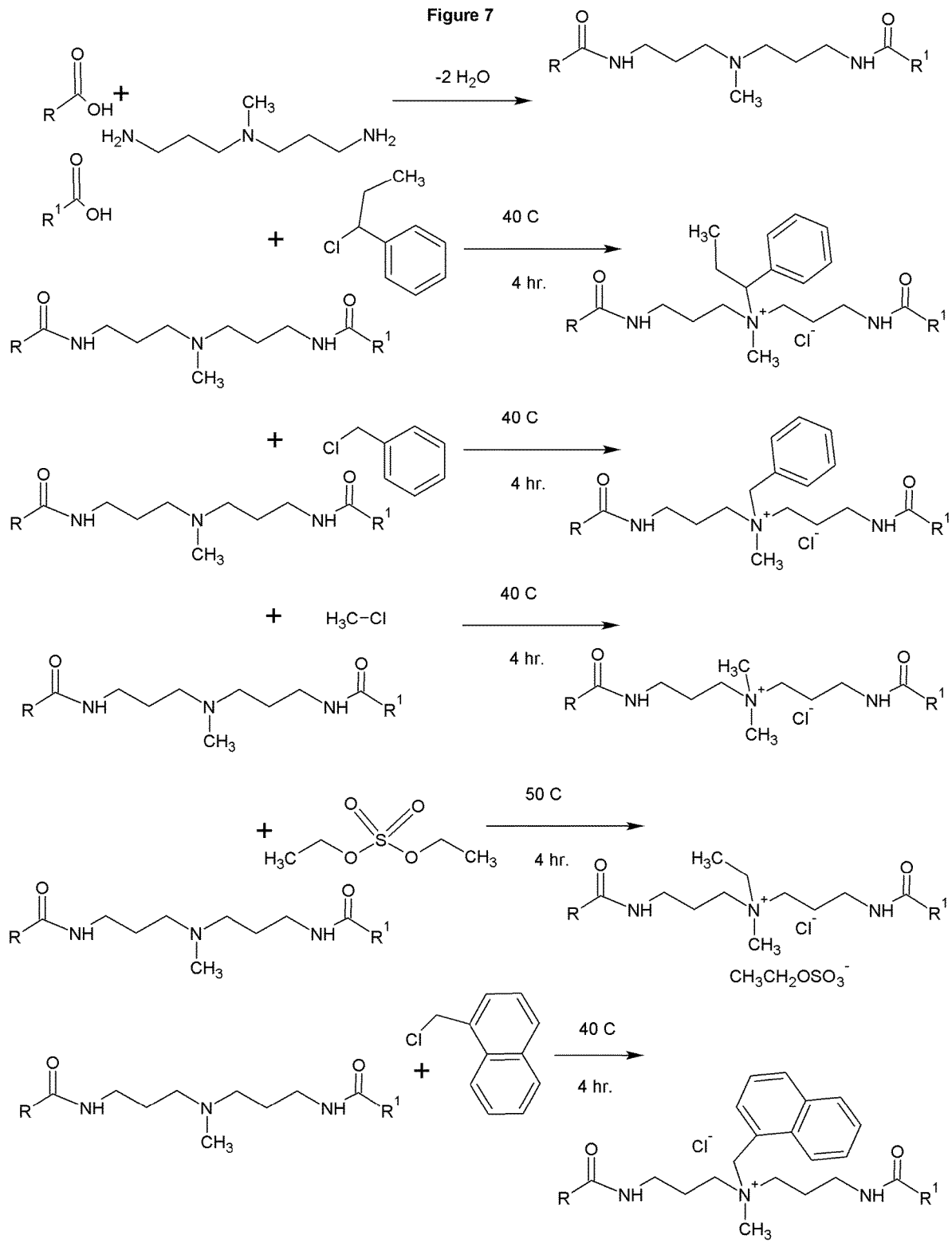
FIG. 7 shows the synthesis of dialkyl quats from N-(3-aminopropyl)-N-methylpropane-1,3-diamine. R and $R^1$ are independently chosen from alkyl, linear or branched, saturated or unsaturated, cyclic or acylic from 1 to 21 carbons.

Another way of achieving dialkyl amidoamine quats is to condense N,N-Bis(2-aminoethyl)methylamine with two moles of fatty acid, followed by quaternization of the tertiary amine as taught in FIG. 6. FIG. 7 shows the synthesis of dialkyl quats from N-(3-aminopropyl)-N-methylpropane-1,3-diamine, which has the advantage of being easier to prepare than N,N-Bis(2-aminoethyl)methylamine. N-(3-aminopropyl)-N-methylpropane-1,3-diamine is readily made in good yield by reacting 2 moles of acrylonitrile with methyl amine and reducing with hydrogen over a sponge nickel catalyst.

The molecules described herein are useful in a range of applications. The molecules find utility as fungicides in personal care as treatments for acne, dandruff, psoriasis, and other fungal skin born conditions, as well as use in feminine products where an antifungal is required that is gentle on the sensitive tissues, as well as HIV prevention. These molecules are also excellent hair conditioners and laundry fabric softeners. Other applications include agriculture as a sporicide, algicide, and fungicide. Oil field applications include treatment of clay to make hydrophilic drilling muds, and in aqueous systems, prevent clay from swelling. In asphalt emulsions as a cationic surfactant.

Several descriptions and illustrations have been presented to enhance understanding of the present invention. One skilled in the art will know that numerous changes and variations are possible without departing from the spirit of the invention. Each of these changes and variations are within the scope of the present invention.

The invention claimed is:

1. A surfactant of the following structure and its salts:

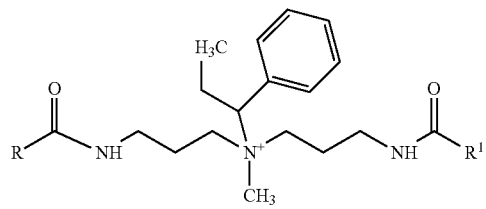

Where R and $R^1$ are independently selected from the group consisting of alkyl, alkenyl, alkynyl, linear or branched, cyclic or acyclic, saturated or unsaturated, from 1 to 22 carbons.

2. A surfactant of claim 1 where at least one of R or $R^1$ is alkyl.

3. A surfactant of claim 1 where R is not equal to $R^1$.

* * * * *